United States Patent [19]

Fabisiewicz

[11] 4,210,479
[45] Jul. 1, 1980

[54] METHOD FOR BONDING A PLASTIC TUBING TO A METAL NEEDLE AND THE NEEDLE ASSEMBLY FORMED THEREBY

[75] Inventor: Eugene Fabisiewicz, Mt. Prospect, Ill.

[73] Assignee: Baxter Travenol Laboratories, Inc., Deerfield, Ill.

[21] Appl. No.: 915,516

[22] Filed: Jun. 14, 1978

[51] Int. Cl.² ............... B29C 19/04; B23K 13/02; H05B 9/04
[52] U.S. Cl. .................. 156/273; 219/10.53; 219/10.81
[58] Field of Search ............... 156/272, 273, 275; 219/10.53, 10.81

[56] References Cited

U.S. PATENT DOCUMENTS

| | | | |
|---|---|---|---|
| 2,542,702 | 2/1951 | Prow | 219/10.53 |
| 2,700,634 | 1/1955 | Ackerlind | 156/273 |
| 3,174,890 | 3/1965 | Goyke | 219/10.53 |
| 3,706,620 | 12/1972 | Dykstra | 156/273 |
| 4,101,356 | 7/1978 | Saveikouis | 156/272 |

*Primary Examiner*—Douglas J. Drummond
*Attorney, Agent, or Firm*—H. W. Collins; Paul Flattery; Thomas Vigil

[57] ABSTRACT

The method for bonding a plastic tubing to a metal needle includes the steps of coating the inner end of the needle with a cement, inserting the coated inner end of the needle within the outer end portion of a plastic tubing and applying a radiofrequency current across the plastic tubing around the inner end of the needle to heat seal the plastic tubing to the inner end of the needle.

20 Claims, 10 Drawing Figures

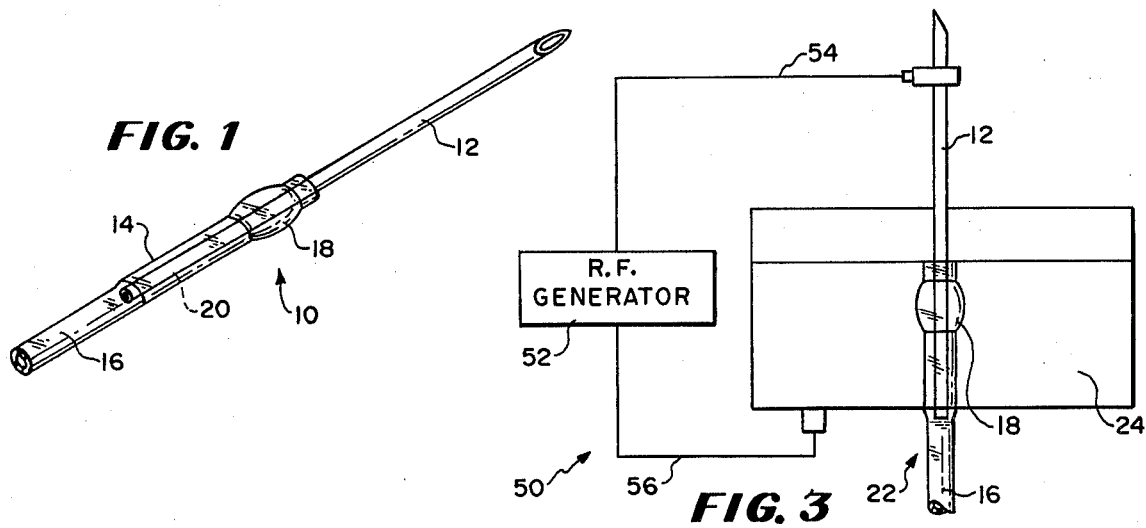
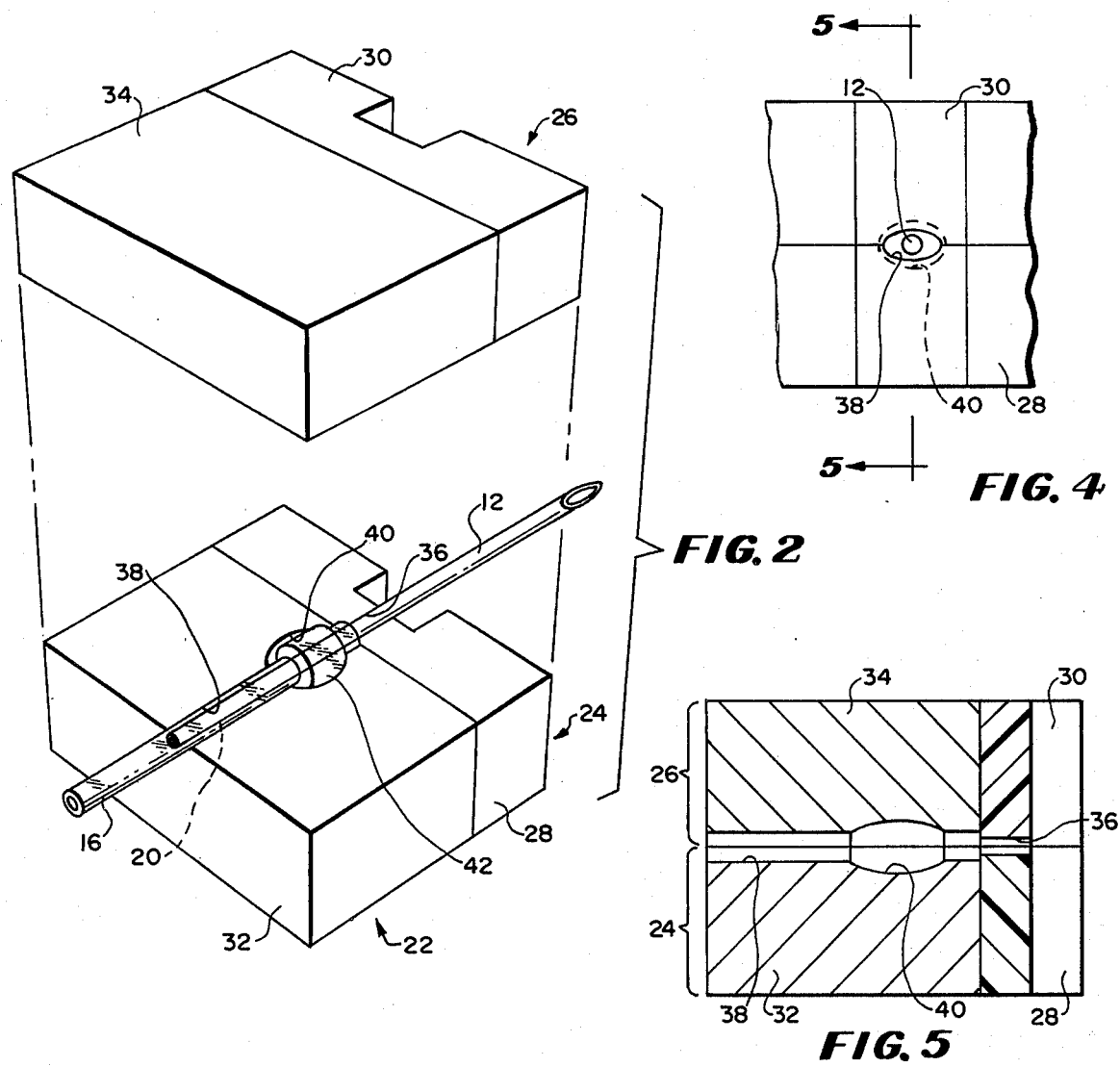

METHOD FOR BONDING A PLASTIC TUBING TO A METAL NEEDLE AND THE NEEDLE ASSEMBLY FORMED THEREBY

BACKGROUND OF THE INVENTION

1. Field of the Invention

The present invention relates to a method and apparatus for bonding a metal needle to a plastic tubing and the needle assembly formed thereby.

2. Description of the Prior Art

Heretofore various techniques have been proposed for securing a needle to a plastic part. Such techniques have included molding a plastic part onto the needle and wedging or swagging a plastic part onto a needle. Examples of such techniques are disclosed in U.S. Pat. Nos. 2,091,438 and 3,964,857.

Also it has been known to use heat sealing techniques for sealing or welding plastic parts together. Examples of such heat sealing techniques are disclosed in U.S. Pat. Nos. 3,300,559, 3,128,504, 3,509,252 and 3,929,943.

Moreover various techniques utilizing an adhesive, heat, solvents or molding techniques for securing a needle to a plastic part have been proposed. Examples of these techniques are disclosed in U.S. Pat. Nos. 3,523,531, 3,523,532, 3,523,533, and 3,640,275.

With the various techniques heretofore proposed there has occurred a problem in the integrity of the bond of the plastic part to the needle. More specifically, the bonds previously achieved by molding, wedging, or using an adhesive, solvent or heat have not provided a strong hermetic seal between the needle and the plastic tubing. Accordingly there was a limitation on the push-pull forces that could be applied to the bond when the needle was inserted or withdrawn from a patient. Also there was a limitation on the pressure of the fluid that could be applied through the tubing and needle assembly. In this respect prior bonds between a needle and a plastic part such as a tubing have not always been able to withstand pressures up to 30 psi.

Another technique heretofore utilized for securing a needle to the end of a plastic tubing was to apply a cement to the inner end of the needle and to apply a solvent such as cyclohexanone to the interior of the tubing. Then the tubing is placed on the end of the needle and the needle assembly formed thereby is placed in a heat chamber to sterilize the needle and at the same time to evaporate the solvent. This technique is slow and cumbersome, often resulted in marring of the outer surface of the tubing with the solvent, and did not provide a bonding having the desired integrity. That is to say, the push-pull strength and the fluid pressure which the resulting needle assembly could withstand did not meet the desired levels.

As will be explained in greater detail hereinafter, the present invention provides a method for bonding the end portion of a plastic tubing to a needle and an apparatus for carrying out the method by means of which a needle assembly is obtained wherein the integrity of the bond between the needle and the plastic tubing has the desired strength and hermetic sealing. More specifically, the needle assembly has a bond which provides a strong mechanical bond and a strong hermetic seal such that the push-pull strength of the needle assembly and the fluid pressure which the needle assembly can withstand meet the levels desired.

SUMMARY OF THE INVENTION

According to the invention there is provided a method for bonding a metal part to a plastic part comprising the steps of: applying a cement to the metal part; placing the metal part in contact with the plastic part; and, applying heat to the portion of the plastic part in contact with the metal part to heat seal the parts together.

Also according to the invention there is provided a method for bonding the end portion of a plastic tubing to a metal needle including the steps of: applying a cement to the inner end of the needle to be inserted within the tubing end portion, placing the needle and tubing within a die comprising two parts, one part being made of an insulating material within which the needle is placed and the other part being metallic within which the tubing end portion is placed, inserting the coated inner end of the needle within the tubing end portion, and applying a high frequency voltage across the outer end of the needle and the metallic part of the die to heat seal the tubing end portion surrounding the coated inner end of the needle to the inner end of the needle.

Further according to the invention there is provided an apparatus for bonding the end portion of a plastic tubing to the inner end of a metal needle comprising a die having two parts, one part being made of insulating material having a cavity within which a portion of the needle is positioned and the other part being a metallic part having a cavity within which the inner end of the needle extends with the end portion of the tubing received over the inner end of the needle and within said metallic part of said die, a source of high frequency voltage and means for connecting the source of high frequency voltage to the outer end of the needle and said metallic part of the die.

Still further according to the invention there is provided a needle assembly comprising a metal needle having an inner end bonded within the end portion of a plastic tubing which is bonded to said inner end of said needle by means of a plastic cement applied to said inner end of said needle and welded to said needle by reason of a high frequency voltage having been applied across said end portion of said plastic tubing received over said inner end of said needle to soften and weld said tubing end portion to said inner end of said needle.

BRIEF DESCRIPTION OF THE DRAWINGS

FIG. 1 is a perspective view of a needle assembly made in accordance with the teachings of the present invention.

FIG. 2 is an exploded perspective view of a die of the apparatus of the present invention in which the needle assembly shown in FIG. 1 is formed.

FIG. 3 is a top plan view of the lower die section of the die shown in FIG. 2 and shows the needle assembly after it has been formed in the die.

FIG. 4 is a fragmentary end view of the needle assembly in the die.

FIG. 5 is a sectional view of the needle assembly and the die and taken along lines 5—5 of FIG. 4.

DESCRIPTION OF THE PREFERRED EMBODIMENTS

Figure 6:
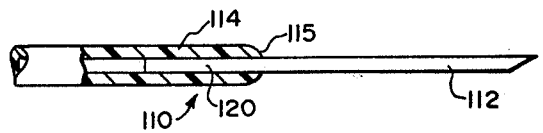
FIG. 6 is a sectional view of another needle assembly made in accordance with the teachings of the present invention.

Referring now to the drawings in greater detail, there is illustrated in FIG. 1 a needle assembly made in accordance with the teachings of the present invention and generally identified by the reference numeral 10. The needle assembly 10 includes a stainless steel needle 12 which is secured to the outer end portion 14 of a plastic tubing 16 which is typically made of polyvinyl chloride or ethylvinyl acetate. Also in this embodiment of the needle assembly 10, an annular bead 18 is formed on the tubing end portion 14 adjacent the outer end thereof to provide an abutment means to facilitate gripping of the needle assembly 10 by a user thereof. Needle assemblies of this type are commonly used for interveneous injections into a patient.

According to the method of the present invention, the inner end 20 of the needle 12 is coated with a vinyl cement such as a cement sold under the tradename CD 203 by Chemical Development Corporation of Danvers, Mass. This cement comprises a resin system including a blend of acrylic and vinyl resins plus a stabilizer together with a solvent system comprising mainly methyl ethyl keytone. Next, the outer end portion 14 of the tubing 16 is inserted over the coated inner end 20 of the needle 12. Then, the tubing end portion 14 is heated to heat seal the tubing end portion 14 to the inner end 20 of the needle 12.

Also, according to the invention, the heat sealing is accomplished by placing the needle assembly 12, prior to sealing, in a die 22 as shown in FIG. 2 and then applying high frequency voltage across the tubing end portion 14. The die 22 has a lower section 24 and an upper section 26. Also, each section 24 and 26 is composed of two parts, one part 28 and 30 respectively, being made of an insulating material such as polytetrafluoroethylene and the other part 32 and 34, respectively, being made of metal such as brass. As shown the parts 28 and 32 are bound together to form the die section 24 and the parts 30 and 34 are bound together to form the die section 26. It will be understood that the die sections 24 and 26 are mirror images of each other and only the lower die section 24 will be described in detail.

The lower die section 24 has a semi-cylindrical cavity 36 formed in the insulative part 28. Axially aligned with this semi-cylindrical cavity 36 is a cavity 38 having a semi-elliptical cross-section in the metal part 32. Additionally, the cavity 38 has a large oval cavity portion 40 situated a short distance from the junction between the parts 24 and 28. As shown the semi-cylindrical cavity 36 is adapted to receive the needle 12 therein whereas the semi-elliptical cross-section cavity 38 is somewhat larger and is adapted to receive the tubing end portion 14 therein prior to the heat sealing. Also, a plastic collar 42 is received about the tubing end portion 14 and positioned within the oval cavity 40. The collar 42 is typically made of the same plastic material as the tubing 16.

It is to be noted that the semi-elliptical cross-section cavity 38 and a similar mating cavity in the upper die section 26 can have other cross sections, e.g., the mating cavities can have a cylindrical cross-section.

An apparatus for carrying out the method includes the die 22 and is generally identified by reference numeral 50 in FIG. 3. The apparatus 50 includes not only the die 22 but also a radio frequency generator 52 which has one output lead 54 connected to the outer end of the needle 12 and another output lead 56 connected to the metal parts 32 and 34 of the die 22. The radio frequency generator 51 used in one embodiment of the apparatus 50 is a two kilowatt generator operating on 220 volts, 60 Hz A.C. and has a variable output voltage at a frequency of 27 MHz. In using the apparatus 50 a radio frequency voltage is applied across the needle 12 and metal parts 32 and 34 for approximately 1½ seconds during which time current flows through the tubing end portion 14 and collar 42 to melt and weld the collar 40 to the tubing end portion 14 to form the bead 18 and to melt and bond the tubing end portion 14 to the inner end 20 of the needle 12.

Figure 8:
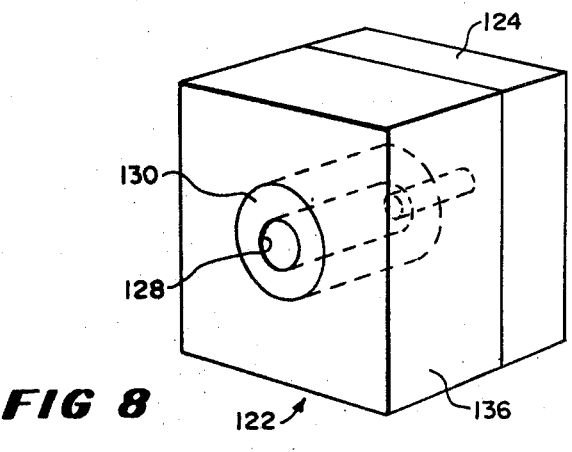
FIG. 8 is an exploded perspective view of the die sections of the apparatus shown in FIG. 7.
Figure 7:
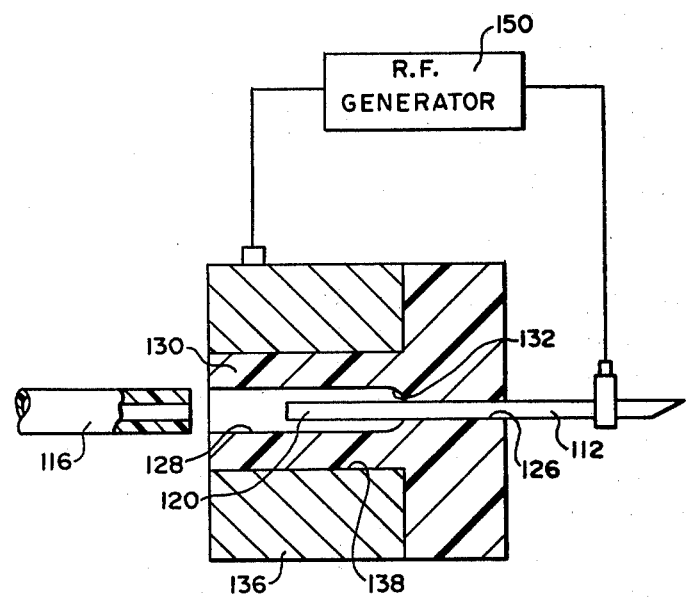
FIG. 7 is a sectional view of the apparatus and die utilized therein for forming the needle assembly shown in FIG. 6.

Referring now to FIGS. 6, 7 and 8, another needle assembly 110 made in accordance with the teachings of the present invention without an annular bead 18 is illustrated in FIG. 6. This needle assembly 110 is referred to as a bullet model since the needle 112 thereof extends from tubing end portion 114 which is rounded at the end 115 thereof. The inner end 120 of the needle 112 is bound to the tubing end portion 114. In this embodiment and as best shown in FIGS. 7 and 8, the needle 112 is first inserted into a die 122 comprising an insulative part 124 which has an aperture 126 therethrough through which the needle 112 is received. The inner end 120 of the needle 112 extends out of the insulative part 124 into a cavity 128 defined within an annular sleeve 130 extending from one side of the insulative part 124 of the die 122. The cavity 120 is generally semi-cylindrical with a rounded bottom 132 as shown.

It will be understood that the generally cylindrical cavity 128 is generally coaxial with the aperture 126.

Surrounding the insulative part 124, which is typically made of polytetrafluoroethylene is a metal part 136 typically made of brass. The metal part 136 has a cylindrical passageway 138 therethrough within which is received the annular sleeve 130 of the insulative part 124. The inner end 120 of the needle 112 is coated with a cement before it is inserted into the die 122 and then the tubing end portion 114 is inserted into the caivity 128 and over the inner end 120 of the needle 112 in the manner indicated in FIG. 7. Next, a radio frequency generator 150 is energized to apply a high frequency voltage across the needle 112 and the metal part 136 so that a high frequency current passes through the tubular end portion 114 for heating, melting and bonding the same to the inner end 120 of the needle 112.

Figure 9:
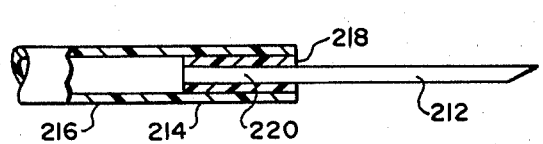
FIG. 9 is a section view of still another needle assembly prior to the bonding of the needle to a bushing and tubing end portion.
Figure 10:
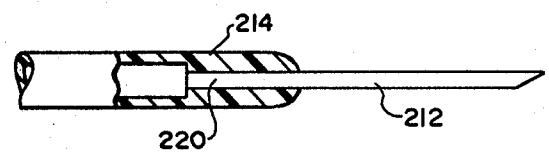
FIG. 10 is a sectional view of the needle shown in FIG. 9 bonded to the bushing and the bushing welded to the tubing end portion after the assembly shown in FIG. 9 has been heat sealed with the apparatus shown in FIG. 7.

Referring to FIGS. 9 and 10 there is illustrated therein another embodiment of the needle assembly of the present invention generally identified by reference numeral 210. In this embodiment, a needle 212 is bonded to the tubing end portion 214 of a plastic tubing 216 which has a larger inner diameter than the outer diameter of the needle 212. This is accomplished by inserting a busing 218 within the outer end of the tubular end portion 214 and then inserting the inner end 220 of the needle 212 into the bushing 218. It will be apparent that the bushing 218 has an outer diameter substantially identical to the inner diameter of the plastic tubing 216 and an inner diameter substantially equal to the outer diameter of the needle 212. This assembly 210 is then inserted into the die 122 and radio frequency voltage is applied across the needle 212 and the metal part 136 to melt and weld the bushing 218 to the tubing end portion 214 and to bond the bushing 218 to the coated end portion 220 of the needle 212.

It has been found that by bonding a needle to a tubing end portion of a plastic tubing in the manner described above using radio frequency heat sealing, a strong bond is obtained which will withstand the push pull forces normally encountered in use of the needle assembly. Also the bond provides a strong hermatic seal which prevents the escape of fluids even at pressures up to 30 psi.

Also, the method and apparatus of the present invention provide a simple, efficient and speedy means for forming a needle assembly having a desired strong bond between a needle and a plastic tubing end portion. Further in this respect, a plurality of dies can be used at one time connected to one R. F. generator to further increase production.

From the foregoing description it will be apparent that the method and apparatus for forming a needle assembly and the needle assembly formed thereby, of the present invention, provide a number of advantages, some of which have been described above and others of which are inherent in the invention. Also, it will be apparent that the obvious modifications can be made to the method and apparatus and assembly formed thereby without departing from the teachings of the present invention. Accordingly, the scope of the present invention is only to be limited as necessitated by the accompanying claims.

I claim:

1. A method for bonding the end portion of a plastic tubing to a metal needle including the steps of: applying a cement to the inner end of the needle to be inserted within the tubing end portion, placing the needle and tubing within a die comprising two parts, one part being made of an insulating material within which the needle is placed and the other part being metallic within which the tubing end portion is placed, inserting the coated inner end of the needle within the tubing end portion, and applying a high frequency voltage across the outer end of the needle and the metallic part of the die to heat seal the tubing end portion surrounding the coated inner end of the needle to the inner end of the needle.

2. The method according to claim 1 wherein a plastic collar is positioned around the tubing end portion near the end thereof to form a bead adjacent the end of the tubing bonded to the needle when the high frequency voltage is applied across the outer end of the needle and the metallic part of the die, the bead providing an abutment means when the end portion of the tubing bonded to the inner end of the needle is gripped by user.

3. The method according to claim 1 wherein the metallic part has a generally cylindrical passage therethrough and the insulative part of the die has a body portion, an annular sleeve portion which has a cavity therein and which extends from the body portion into the generally cylindrical passage and an aperture through the body portion coaxial with the annular portion and wherein the needle is first placed in the aperture with the inner end of the needle extending into the cavity followed by coating the inner end of the needle, inserting the end of the plastic tubing over the coated inner end of the needle and then applying a radiofrequency voltage across the needle and metallic part of the die 4. The method according to claim 1 wherein the tubing is larger than the needle and a bushing having an inner diameter substantially equal to the outer diameter of the needle is first inserted into the inner end of the plastic tubing after which the inner end of the needle is coated and inserted into the bushing followed by placing the needle and bushing into the die and then applying high frequency voltage across the outer end of the needle and the metallic part of the die to bond the bushing to the plastic tubing and to the needle.

5. The method according to claim 1 wherein said high frequency voltage is obtained from a radiofrequency generator.

6. The method according to claim 5 wherein the frequency is approximately 27 mHz.

7. The method according to claim 5 wherein the radiofrequency generator has a power capacity of approximately 2 kW.

8. The method according to claim 1 wherein the high frequency voltage is applied to the outer end of the needle and the metallic part of the die for approximately $1\frac{1}{2}$ seconds.

9. The method according to claim 1 wherein the inner end of the needle is coated with cement formed from a resin system including a blend of acrylic and vinyl resins plus a stabilizer and a solvent system comprising methyl ethyl ketone.

10. The method according to claim 1 being carried out with a die wherein the insulating part is made of polytetrafluoroethylene and the metallic part is made of brass.

11. The method according to claim 1 wherein wherein the inner end of the needle is inserted in the end portion of the tubing before the needle and tubing end portion are placed in the die.

12. The method according to claim 1 wherein the needle is first placed in the die and then the tubing end portion is placed in the die over the inner end of the needle.

13. The method according to claim 1 wherein the tubing is made of polyvinyl chloride.

14. The method according to claim 1 wherein the tubing is made of ethyl vinyl acetate.

15. The method according to claim 1 wherein the needle is made of stainless steel.

16. A method for bonding a stainless steel needle to plastic tubing comprising the steps of:
    applying cement to a portion of the stainless steel needle;
    placing said portion of the stainless steel needle in contact with a segment of the plastic tubing;
    placing said portion of said needle and said segment of plastic tubing in a metal die member substantially surrounding said segment of the plastic tubing in contact with said needle; and
    applying heat to said segment of the plastic tubing in contact with the stainless steel needle by applying a high frequency current between said needle and said metal die member to seal the needle and the tubing together.

17. The method according to claim 16 wherein the frequency of the current is approximately 27 mHz.

18. The method according to claim 16 wherein the plastic tubing is made of polyvinyl chloride.

19. The method according to claim 16 wherein the plastic part tubing is made of ethyl vinyl acetate.

20. The method according to claim 18 or 19 wherein the cement is formed from a resin system including a blend of acrylic and vinyl resins plus a stabilizer and a solvent system comprising methyl ethyl ketone.

* * * * *